US009412393B2

(12) United States Patent
Spizzo et al.

(10) Patent No.: US 9,412,393 B2
(45) Date of Patent: Aug. 9, 2016

(54) SPEECH EFFECTIVENESS RATING

(71) Applicant: International Business Machines Corporation, Armonk, NY (US)

(72) Inventors: Patrick A. Spizzo, Oak Brook, IL (US); Sara H. Waggoner, Bradenton, FL (US); Kaleb D. Walton, Fenton, MI (US); Aaron T. Wodrich, Westminster, CO (US)

(73) Assignee: International Business Machines Corporation, Armonk, NY (US)

( * ) Notice: Subject to any disclaimer, the term of this patent is extended or adjusted under 35 U.S.C. 154(b) by 100 days.

(21) Appl. No.: 14/260,757

(22) Filed: Apr. 24, 2014

(65) Prior Publication Data

US 2015/0310852 A1  Oct. 29, 2015

(51) Int. Cl.
   *G10L 15/08*   (2006.01)
   *G10L 25/48*   (2013.01)
   *G10L 15/18*   (2013.01)

(52) U.S. Cl.
   CPC .................. *G10L 25/48* (2013.01); *G10L 15/08* (2013.01); *G10L 15/1822* (2013.01)

(58) Field of Classification Search
   CPC .................................. G10L 15/08; G10L 25/48
   USPC ......................................................... 704/251
   See application file for complete search history.

(56) References Cited

U.S. PATENT DOCUMENTS

| 5,634,086 | A | 5/1997 | Rtischev et al. |
| 5,794,203 | A | 8/1998 | Kehoe |
| 7,840,404 | B2 | 11/2010 | Xi et al. |
| 8,036,899 | B2 | 10/2011 | Sobol-Shikler |
| 8,209,714 | B2 * | 6/2012 | de los Reyes ...... H04N 21/4425 725/107 |
| 8,386,252 | B2 | 2/2013 | Michaelis |
| 8,595,015 | B2 | 11/2013 | Lee et al. |
| 2002/0099554 | A1 * | 7/2002 | Spiser-Albert ........... G09B 5/06 704/271 |
| 2003/0202007 | A1 | 10/2003 | Silverstein et al. |
| 2007/0100626 | A1 | 5/2007 | Miller et al. |
| 2008/0159560 | A1 * | 7/2008 | Song ....................... G10L 25/78 381/94.1 |

(Continued)

OTHER PUBLICATIONS

Brooyat, "Hard of Hearing", Voice and Speech Systems, No. 53, Copyright 2014, <http://voiceandspeechsystems.com/index.php/hard-of-hearing/>.

(Continued)

*Primary Examiner* — James Wozniak
*Assistant Examiner* — Oluwadamilola M Ogunbiyi
(74) *Attorney, Agent, or Firm* — Maeve Carpenter

(57) ABSTRACT

In an approach to determining speech effectiveness, a computer receives speech input. The computer determines, based, at least in part, on the received speech input, whether the speech input is one of: a conversation with words spoken by two or more people during a predetermined time interval, and a presentation with words spoken by one person and not any other person during a predetermined time interval. The computer detects at least one problem with the speech input. If the speech input is the presentation, the computer weights, by a first factor, the detected at least one problem with the speech input based on the speech input being a presentation and not a conversation, and if the speech input is a conversation, the computer weights, by a second factor, the detected at least one problem with the speech input based on the speech input being a conversation and not a presentation.

17 Claims, 4 Drawing Sheets

(56) References Cited

U.S. PATENT DOCUMENTS

| | | | |
|---|---|---|---|
| 2010/0274554 A1* | 10/2010 | Orr | G10L 25/93 704/201 |
| 2011/0040554 A1* | 2/2011 | Audhkhasi | G09B 19/04 704/9 |
| 2011/0213610 A1* | 9/2011 | Chen | G06F 17/2715 704/9 |
| 2011/0295597 A1 | 12/2011 | Brady | |
| 2012/0164612 A1* | 6/2012 | Gillick | G09B 19/04 434/185 |
| 2012/0203545 A1 | 8/2012 | Shaw | |
| 2013/0185057 A1 | 7/2013 | Yoon et al. | |
| 2013/0201272 A1* | 8/2013 | Enbom | H04M 3/567 348/14.01 |
| 2013/0304472 A1* | 11/2013 | Pakhomov | G10L 15/005 704/254 |
| 2014/0278421 A1* | 9/2014 | Komissarchik | G09B 19/06 704/251 |

OTHER PUBLICATIONS

Kaushik et al., "Automatic Detection and Removal of Disfluencies from Spontaneous Speech", SST, pp. 98-101, Dec. 14-16, 2010.

Nahmoo, "Analytics Education: Sound and Speech Analytics", SmarterAnalytics, IBM, Sep. 2013.

* cited by examiner

| SPEECH PROBLEM | WEIGHT BY SPEAKING MODE | | THRESHOLD BASIS | | | THRESHOLDS BY SPEAKING MODE | | |
|---|---|---|---|---|---|---|---|---|
| | GROUP | ONE ON ONE | PRESENTATION | BASE VALUE | UNIT | GROUP | ONE ON ONE | PRESENTATION |
| ANGER | 2 | 3 | 1 | 15 | SECONDS | 30 | 45 | 15 |
| BACKGROUND NOISE | 2 | 3 | 1 | 30 | SECONDS | 60 | 90 | 30 |
| FALSE STARTS | 2 | 3 | 1 | 2 | INCIDENTS | 4 | 6 | 2 |
| FAST TALKING | 2 | 3 | 1 | 15 | SECONDS | 30 | 45 | 15 |
| FILIBUSTERING | 1 | 2 | N/A | 60 | SECONDS | 60 | 120 | N/A |
| FILLERS | 2 | 2 | 1 | 3 | INCIDENTS | 6 | 6 | 3 |
| INTERRUPTING | 2 | 1 | N/A | 1 | INCIDENTS | 2 | 1 | N/A |
| MUMBLING | 2 | 3 | 1 | 5 | INCIDENTS | 10 | 15 | 5 |
| REPAIRED UTTERANCES | 2 | 3 | 1 | 2 | INCIDENTS | 4 | 6 | 2 |
| SHOUTING | 2 | 1 | 3 | 2 | INCIDENTS | 4 | 2 | 6 |
| SLOW TALKING | 2 | 2 | 3 | 15 | SECONDS | 30 | 30 | 45 |
| STRESS | 1 | 1 | 3 | 15 | SECONDS | 15 | 15 | 45 |
| TALKING OVER | 1 | 1 | N/A | 1 | INCIDENTS | 1 | 1 | N/A |

LEGEND
WEIGHTS:
1=HIGH
2=MEDIUM
3=LOW

BASE TIME PERIOD:
5 MINUTES

FIG. 3

SPEECH EFFECTIVENESS RATING

FIELD OF THE INVENTION

The present invention relates generally to the field of speech analysis, and more specifically to evaluation and rating of speech effectiveness.

BACKGROUND

The ability to effectively communicate information using speech remains a challenge for many individuals. One problem may be with speech disfluencies. A speech disfluency is any of various breaks, irregularities, or non-lexical vocables that occurs within the flow of otherwise fluent speech. These include false starts, i.e. words and sentences that are cut off mid-utterance, phrases that are restarted or repeated and repeated syllables, fillers, i.e. grunts or non-lexical utterances such as "huh", "uh", "erm" and "well", and repaired utterances, i.e. instances of speakers correcting their own slips of the tongue or mispronunciations. In addition to speech disfluencies, other problems, such as interrupting, fast talking, mumbling, and shouting, can result in consequences that can have a long term effect on a person's career or personal life. As more work is done remotely, e.g., via conference calls, on-line broadcasts, etc., the ability to effectively speak becomes even more important as visual body language cues are removed from the communication process. Instead, listeners concentrate their focus on the speaker's voice, grammar, and audible style.

Current methods of teaching public speaking, teaching proper speaking, or improving speech problems require humans to detect problems and provide all of the feedback. Typically, speech training is done in person, where the speech is often not recorded or analyzed specifically to review later. Even if the speech is recorded or notes are documented, feedback is typically obtained through a manual process, and the feedback is not typically linked directly with different portions of speech. Real-time analysis is more difficult to provide, as feedback is typically not available without interrupting the speaker.

U.S. Pat. No. 8,595,015 B2 by Lee, et al., describes a device for audio communication assessment. The device includes a communication interface configured to receive audio signals associated with audible communications from a user, an output device, and logic. The logic is configured to determine one or more audio qualities associated with the audio signals, map the one or more audio qualities to at least one value, generate audio-related information based on the mapping, and provide, via the output device during the audible communications, the audio-related information to the user.

SUMMARY

Embodiments of the present invention disclose a method, computer program product, and system for determining speech effectiveness. The method includes one or more computer processors receiving speech input. The one or more computer processors determine, based, at least in part, on the received speech input, whether the speech input is one of: a conversation with words spoken by two or more people during a predetermined time interval, and a presentation with words spoken by one person and not any other person during a predetermined time interval. The one or more computer processors detect at least one problem with the speech input. If the speech input is the presentation, the one or more computer processors weight, by a first factor, the detected at least one problem with the speech input based on the speech input being a presentation and not a conversation, and if the speech input is a conversation, the one or more computer processors weight, by a second factor, the detected at least one problem with the speech input based on the speech input being a conversation and not a presentation.

BRIEF DESCRIPTION OF THE SEVERAL VIEWS OF THE DRAWINGS

FIG. 3 illustrates an example of pre-defined criteria for rating speech effectiveness, in accordance with an embodiment of the present invention.

DETAILED DESCRIPTION

Embodiments of the present invention recognize that improvements to speech effectiveness can be made by detecting speech problems and providing constructive feedback to the speaker. Implementation of embodiments of the invention may take a variety of forms, and exemplary implementation details are discussed subsequently with reference to the Figures.

Figure 1:
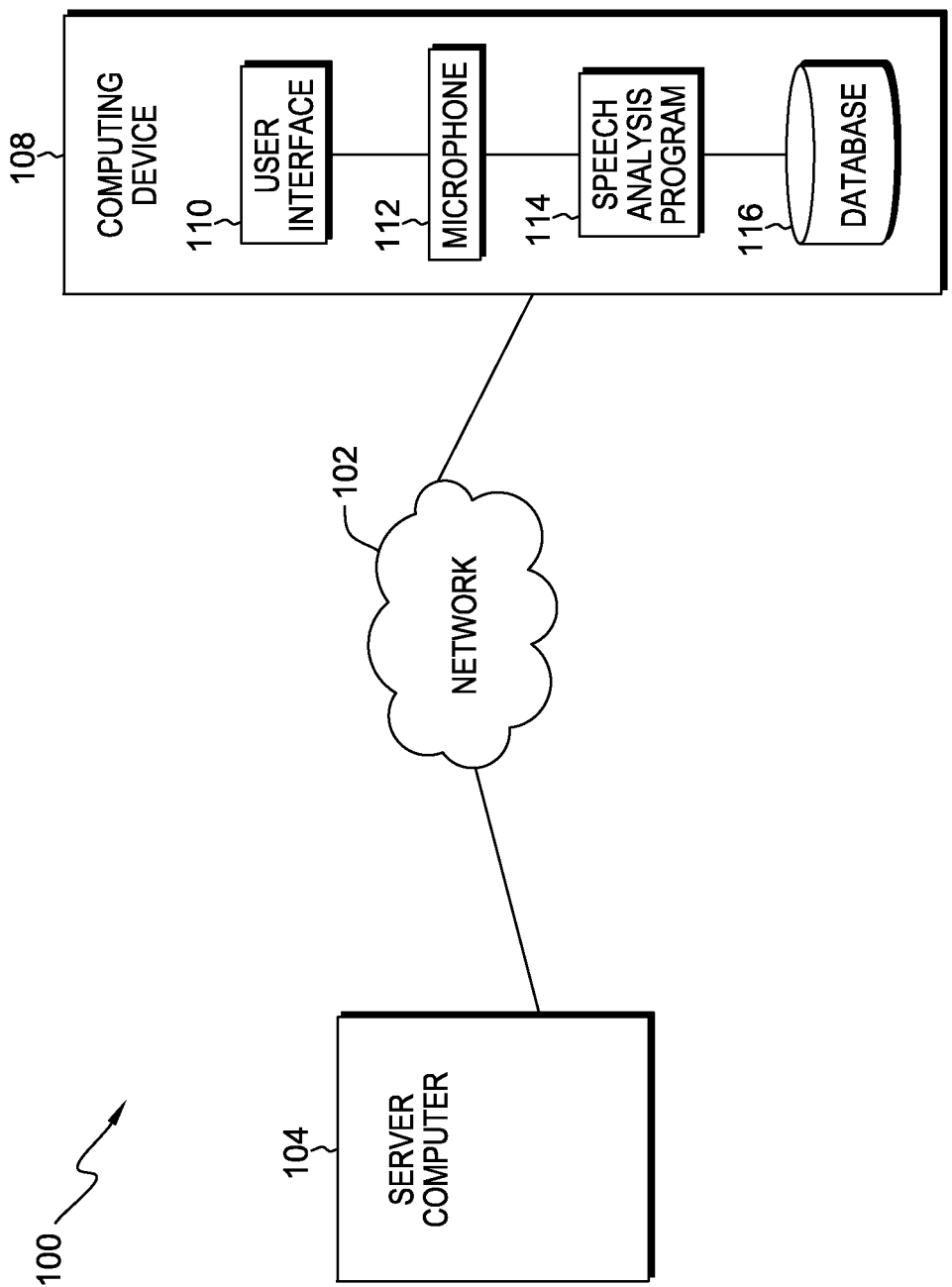
FIG. 1 is a functional block diagram illustrating a distributed data processing environment, in accordance with an embodiment of the present invention.

The present invention will now be described in detail with reference to the Figures. FIG. 1 is a functional block diagram illustrating a distributed data processing environment, generally designated 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes server computer 104 and computing device 108, interconnected over network 102. Network 102 can be, for example, a telecommunications network, a local area network (LAN), a wide area network (WAN), such as the Internet, or a combination of the three, and can include wired, wireless, or fiber optic connections. Network 102 may include one or more wired and/or wireless networks that are capable of receiving and transmitting data, voice, and/or video signals, including multimedia signals that include voice, data, and video information. For example, network 102 may include one or more public switched telephone networks (PSTNs) or other type of switched network. Network 102 may also include one or more wireless networks and may include a number of transmission towers for receiving wireless signals and forwarding the wireless signals toward the intended destinations. In general, network 102 can be any combination of connections and protocols that will support communications between server computer 104 and computing device 108.

Server computer 104 may be a management server, a web server, or any other electronic device or computing system capable of receiving and sending data. In other embodiments, server computer 104 may represent a server computing system utilizing multiple computers as a server system, such as in a cloud computing environment. In another embodiment, server computer 104 may be a laptop computer, a tablet computer, a netbook computer, a personal computer (PC), a desktop computer, a personal digital assistant (PDA), a smart phone, or any programmable electronic device capable of communicating with computing device 108 via network 102. In another embodiment, server computer 104 represents a computing system utilizing clustered computers and components to act as a single pool of seamless resources.

Computing device 108 may be a desktop computer, a laptop computer, a tablet computer, a specialized computer server, a smart phone, or any programmable electronic device capable of communicating with server computer 104 via network 102 and with various components and devices within distributed data processing environment 100. Computing device 108 may be a wearable computer. Wearable computers are miniature electronic devices that may be worn by the bearer under, with or on top of clothing, as well as in glasses, hats, or other accessories. Wearable computers are especially useful for applications that require more complex computational support than just hardware coded logics. In general, computing device 108 represents any programmable electronic device or combination of programmable electronic devices capable of executing machine readable program instructions and communicating with other computing devices via a network, such as network 102. Computing device 108 includes user interface 110, microphone 112, speech analysis program 114, and database 116.

User interface 110 is a program that provides an interface between a user of computing device 108 and speech analysis program 114. A user interface, such as user interface 110, refers to the information (such as graphic, text, and sound) that a program presents to a user and the control sequences the user employs to control the program. There are many known types of user interfaces. In one embodiment, user interface 110 is a graphical user interface. A graphical user interface (GUI) is a type of user interface that allows users to interact with electronic devices, such as a computer keyboard and mouse, through graphical icons and visual indicators, such as secondary notation, as opposed to text-based interfaces, typed command labels, or text navigation. In computing, GUIs were introduced in reaction to the perceived steep learning curve of command-line interfaces which require commands to be typed on the keyboard. The actions in GUIs are often performed through direct manipulation of the graphical elements. In one embodiment, user interface 110 is the interface between computing device 108 and speech analysis program 114. In other embodiments, user interface 110 provides an interface between speech analysis program 114 and server computer 104.

Microphone 112 receives sounds from one or more speakers. A microphone is an acoustic-to-electric transducer or sensor that converts sound in air into an electrical signal. Sounds may include the voice of the user of computing device 108 as well as voices of one or more speakers with which the user of computing device 108 is speaking. Sounds may also include background noises. In one embodiment, microphone 112 resides in computing device 108. In another embodiment, microphone 112 may reside in a second computing device, such as a telephone, provided the second computing device can communicate with computing device 108. In a further embodiment, microphone 112 may be a stand-alone microphone placed in a room where the user is speaking, provided the stand-alone microphone can communicate with computing device 108. Microphone 112 may represent one or more microphones.

Speech analysis program 114 detects, analyzes, rates, and provides real time notification of problems with various qualities of speech effectiveness. It should be understood that the term "speech" as used herein may refer to any form of verbal communication, including free form speech, scripted speech, conversation, etc. Speech analysis program 114 also detects speaking mode or speech input type. For example, speech analysis program 114 can determine whether a speaker is in a one on one conversation, a group conversation, or giving a presentation. Speech analysis program 114 determines the speaking mode, and rates speech problems according to that mode. Speech analysis program 114 may also determine when a speaking mode changes, and changes the analysis and ratings appropriately. Speech analysis program 114 may notify the user in real time of speech problems that need immediate attention. Speech analysis program 114 utilizes voice recognition analytics to detect the voices of various speakers. As will be appreciated by one skilled in the art, multiple voice recognition techniques exist which can be utilized by speech analysis program 114 for performing voice recognition. For example, a voice sample is converted from an analog format to a digital format, the features of the individual's voice are extracted, and a model is created. Many speaker verification systems use the concept of Hidden Markov Models (HMMs) that provide a statistical representation of the sounds produced by an individual. The HMM represents the underlying variations and temporal changes over time found in the speech states using quality, duration, intensity dynamics, and pitch characteristics. Speech analysis program 114 also stores speech analyses in order to provide the user with reports of ongoing speaking trends. A user may request to view a stored analysis, via user interface 110. In one embodiment, speech analysis program 114 resides on computing device 108. In another embodiment, speech analysis program 114 may reside in server computer 104 or elsewhere in the environment. Speech analysis program 114 is depicted and described in further detail with respect to FIG. 2.

Database 116 resides on computing device 108. In another embodiment, database 116 may reside on server computer 104, or elsewhere in the environment. A database is an organized collection of data. Database 116 can be implemented with any type of storage device capable of storing data that may be accessed and utilized by computing device 108, such as a database server, a hard disk drive, or a flash memory. In other embodiments, database 116 can represent multiple storage devices within computing device 108. Database 116 is used to store speech analyses produced by speech analysis program 114. In another embodiment, database 116 stores pre-defined criteria for analyzing speech problems. Pre-defined criteria may include weight factors for rating speech problems, and base and threshold values of time intervals and incidents for speech analysis program 114 to determine whether or not to notify the user of speech effectiveness problems. In yet another embodiment, database 116 stores user defined criteria for analyzing speech problems. A user may have preferences for speaking mode or problems to be analyzed. The user can, via user interface 110, edit pre-defined criteria in database 116, and/or enter new criteria to be used by speech analysis program 114. Database 116 may also store information regarding voice recognition. For example, a user can store a sample of a specific speaker's voice and associate the sample with the speaker's name. Speech analysis program 114 can retrieve the voice sample information from database 116 to enhance the analysis.

Figure 2:
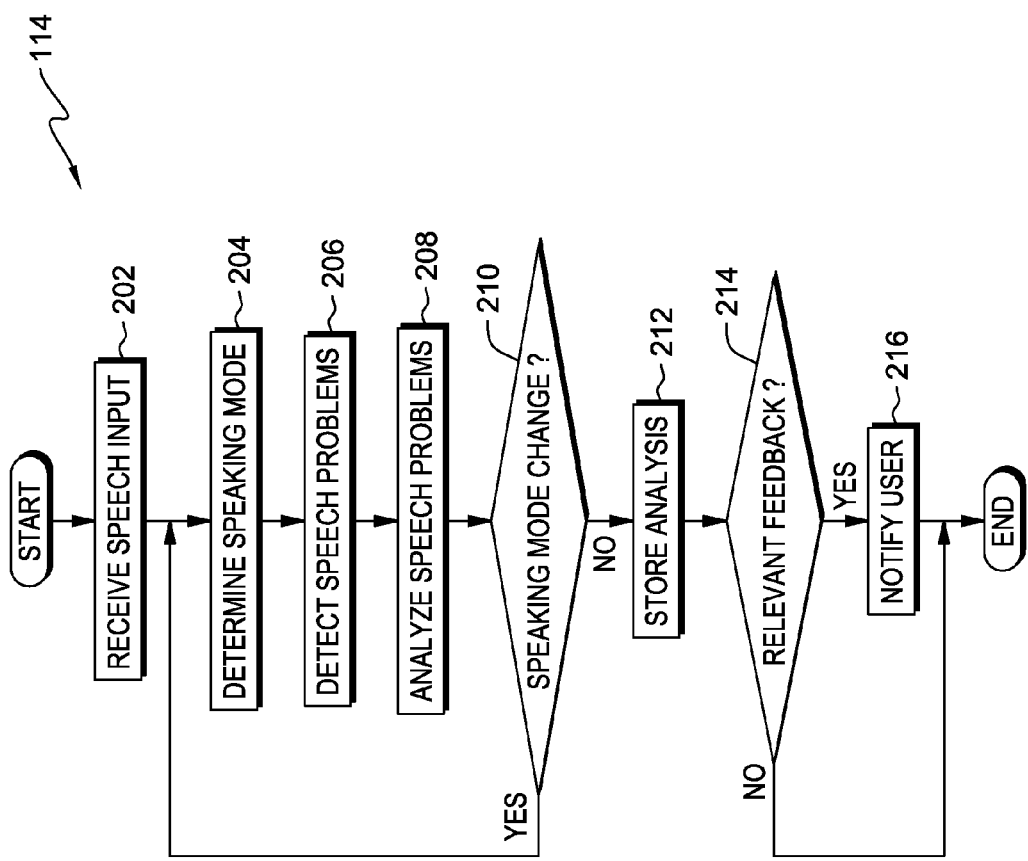
FIG. 2 is a flowchart depicting operational steps of a speech analysis program, on a computing device within the data processing environment of FIG. 1, for analyzing speech effectiveness, in accordance with an embodiment of the present invention.

FIG. 2 is a flowchart depicting operational steps of speech analysis program 114, on computing device 108 within data processing environment 100 of FIG. 1, for analyzing speech effectiveness, in accordance with an embodiment of the present invention.

Speech analysis program 114 receives speech input from microphone 112 (step 202). A user interested in receiving feedback on speech effectiveness initiates speech analysis program 114, such that microphone 112 receives the sound of the user speaking, converts the sound to electrical signals, and sends the signals to speech analysis program 114. Speech analysis program 114 may also receive other sounds, such as background noise. For example, if a dog is barking near where the user is speaking, speech analysis program 114 receives the barking sound along with the speech input.

Speech analysis program 114 determines a speaking mode (step 204). A speaking mode represents a different situation where a user may have different speech patterns. A user may speak one on one with another individual, where the speaking goes back and forth between the two speakers. A one on one conversation may take place either face to face or through a device, such as a telephone. A user may speak in a group discussion where various speakers take turns speaking and asking questions. A group discussion can occur face to face or through a device, such as a telephone, or through a combination of both. A user may be giving a presentation to one or more listeners, where the user is the only individual speaking. Each of the aforementioned speaking modes have specific characteristics that can be detected by speech analysis program 114 over a defined base period of time. For example, speech analysis program 114 may detect the user's voice as well as one other voice in a predetermined period such as a five minute period of time. In this example, speech analysis program 114 determines that the user is in one on one discussion/conversation mode. In another example, speech analysis program 114 may detect multiple voices in a predetermined period such as a five minute period of time. In this example, speech analysis program 114 determines that the user is in group discussion/conversation mode. In yet another example, speech analysis program 114 may detect only the user's voice in a predetermined period such as a five minute period of time. In this example, speech analysis program 114 determines that the user is in presentation mode, where a user is giving a presentation to listeners. In another embodiment, the user can enter the speaking mode, via user interface 110, and set speech analysis program 114 to the appropriate speaking mode for the situation.

Speech analysis program 114 detects speech problems (step 206). Speech problems that speech analysis program 114 may detect belong to several categories. Speech problem categories include courtesy problems, presentation problems, emotional alarms, speech disfluencies, and background noise.

Courtesy problems may include shouting, interrupting, talking over, and filibustering (in a discussion mode). For example, shouting may be detected by tracking a baseline voice level for each speaker throughout a conversation. When a voice level is detected as elevated past a defined threshold, for example, 150% of the baseline, the voice is considered to be shouting. Interrupting may be detected when, for example, Speaker A is talking, and within a defined threshold between words, for example 0 to 50 milliseconds, Speaker B begins talking. Speaker A and Speaker B have a speaking collision where both voices are detected at the same time, and Speaker B is considered the interrupter. If, in the previous example, following an interruption, both Speaker A and Speaker B sustain speaking for a defined interval of time, for example 5 seconds, the event may be considered talking over. Filibustering may be detected, for example, when, in a conversation between two or more speakers, only one voice is detected over a defined time interval.

Presentation problems may include fast talking, slow talking, mumbling, and shouting. Fast talking and slow talking may be detected by comparing a speaker's rate of speech to a baseline based on a language. For example, a baseline of average spoken words per minute is calculated, and thresholds are defined for both fast and slow talking. If a speaker's spoken words per minute exceed the upper limit threshold for spoken words per minute, then fast talking is detected. If a speaker's spoken words per minute are lower than the lower threshold for spoken words per minute, then slow talking is detected. Mumbling may be detected similarly to the detection of shouting, described earlier. A baseline voice level is tracked for each speaker throughout a conversation. When a voice level is detected as lowered below a defined threshold, for example, 50% of the baseline, the voice is considered to be mumbling.

Emotional alarms include stress and anger undertones recognizable in the user's speech. Multiple techniques exist to detect emotional content in speech, including Natural Language Processing (NLP) techniques that may detect "angry words", as well as known techniques for analyzing acoustic features such as pitch, intensity, and energy. For example, the combination of acoustic and prosodic information can be integrated into a HMM-based speech recognition system to detect the emotional state of a speaker. Prosodic information includes patterns of stress and intonation in a language.

Speech disfluencies include the use of fillers, such as "um" or "uh", repaired utterances, such as "brought, I mean bought", and false starts, such as "well if . . . well if I did this". Speech analysis program 114 has been preprogrammed to recognize "um" and "uh" utterances by their sound. An example of a technique for detecting repaired utterances is a word spotting technique based on dynamic time warping (DTW) and N-best hypotheses overlapping measure.

Background noises include, for example, a dog barking, a baby crying, and unrelated conversations. In one embodiment, background noises are any sounds that are not identifiable as voices in the current conversation. In another embodiment, samples of typical background noises are stored in database 116 such that speech analysis program 114 can compare detected background noise to the samples in the database for identification purposes.

In addition to speech problems, speech analysis program 114 may also detect speech factors considered to be positive aspects of speech. For example, as discussed earlier, speech analysis program 114 may detect courtesy problems, however speech analysis program 114 may also detect courtesy enhancements, such as a speaker saying "please", "thank you" or "excuse me".

Speech analysis program 114 quantifies the speech problems, for example with a rating system (step 208). For example, for each detected speech problem in each detectable speech problem category, speech analysis program 114 counts the number of detected speech problems per predetermined time interval and applies a weighted score. Speech analysis program 114 recognizes speech problems based on the determined speaking mode. For example, if the user is speaking in presentation mode, then speech analysis program 114 ignores filibustering or shouting, but considers and weights heavily mumbling, fillers, and false starts. In another example, if the user is in "one on one" mode, then speech analysis program 114 reduces the weight of problems such as fillers. In yet another example, if the user is in group discussion mode, then speech analysis program 114 increases the weight of speech problems such as anger and filibustering. In one embodiment, speech analysis program 114 compares the score of each detected speech problem to a pre-defined threshold and base time interval to determine whether, within the rating system, the detected speech problem may be affecting the user's speech effectiveness. In another embodiment, the user can customize the thresholds and base time interval, via user interface 110. For example, a user may want to highlight one or more particular speech problems that need improvement, and therefore changes the pre-defined weight factors. In another example, a user may pre-set the thresholds and base time periods of speech analysis program 114 to span a particular day where the user may have various one on one meetings, group discussions and presentations.

Speech analysis program 114 determines if the speaking mode has changed (decision block 210). Speech analysis program 114 may determine that the speaking mode has changed after analyzing the user's speech for a predetermined time interval. For example, if speech analysis program 114 defaults to one on one speaking mode and a base time period of five minutes, and the user is giving a presentation, then speech analysis program 114 may detect filibustering as a speech problem because only one voice is detected for a period of five minutes. If speech analysis program 114 continues to only detect one voice, then speech analysis program 114 determines that the speaking mode has changed from one on one mode to presentation mode. In another embodiment, the user of computing device 108 can, via user interface 110, set the speaking mode to the appropriate mode. For example, if the user calls in to a group discussion, the user can set speech analysis program 114 to group discussion mode at the beginning of the call. If speech analysis program 114 determines that the speaking mode has changed (yes branch, decision block 210), then speech analysis program 114 returns to step 204 and determines the new speaking mode.

If speech analysis program 114 determines that the speaking mode has not changed (no branch, decision block 210), then speech analysis program 114 stores the analysis (step 212). Speech analysis program 114 stores the analysis for reporting feedback over a period of time. For example, a user may want to determine whether any improvement has been made in the number of times the user interrupts another speaker while in one on one speaking mode over a period of three months. In another example, a user may want to review speech effectiveness trends of a regularly scheduled group discussion in order to provide feedback to members of the group. Speech analysis program 114 stores the analyses produced over time such that the user can compare the analyses, via user interface 110, and look for trends, both positive and negative. In one embodiment, speech analysis program 114 stores the analyses in database 116. In another embodiment, speech analysis program 114 stores the analyses in a data storage device on server computer 104 via network 102.

Speech analysis program 114 determines whether there is any relevant feedback from the speech problem analysis to provide to the user (decision block 214). If speech analysis program 114 determines that there is no relevant feedback (no branch, decision block 214) because none of the detected speech problems exceed the pre-defined thresholds, then speech analysis program 114 ends.

If speech analysis program 114 determines that there is relevant feedback (yes branch, decision block 214), then speech analysis program 114 notifies the user (step 216). Speech analysis program 114 notifies the user of relevant feedback regarding speech effectiveness and speech problems. In one embodiment, the notification includes the relevant feedback. For example, if the notification is in real time during a conversation, speech analysis program 114 notifies the user of currently detected speech problems. In another embodiment, the notification tells the user that feedback is available for viewing. For example, if the notification is for a monthly report, speech analysis program 114 notifies the user that the report is available for viewing, via user interface 110. In one embodiment, where computing device 108 is a wearable computer embedded in eye glasses, and the user is giving a presentation, speech analysis program 114 notifies the user by displaying messages in the corner of a lens of the eye glasses, such that only the user sees the feedback. In another embodiment, where computing device 108 is a laptop, and the user is in a group discussion on a conference call, speech analysis program 114 may notify the user by displaying messages on the laptop screen. In a further embodiment, where computing device 108 is a smart phone, and the user is in a face to face, one on one, conversation, speech analysis program 114 may notify the user of specific speech problems by vibrating in a particular pattern. In one embodiment, speech analysis program 114 notifies the user in real time. For example, a user is giving a presentation, and computing device 108 is a smart phone that the user has placed on the podium. If speech analysis program 114 detects speech problems, such as fillers, speech analysis program 114 may display a message on the smart phone screen that says "SAYING UM TOO MUCH." In another embodiment, a user is in a group discussion, and speech analysis program 114 may be set, via user interface 110, to notify in an audible, simulated voice, such that, in addition to the user, other participants in the discussion can benefit from the analysis. For example, if speech analysis program 114 detected interruptions in a group discussion, speech analysis program 114 may notify all members of the group by saying, "Interruption detected. Please let the speaker finish before talking." In another embodiment, speech analysis program 114 provides feedback that may be based on data retrieved over a period of time. For example, the user of computing device 108 may set speech analysis program 114, via user interface 110, to provide a monthly or quarterly report on speech effectiveness in group discussions. Speech analysis program 114 may retrieve the stored analyses from database 116 from the last month and summarize the occurrences of various speech problems detected during the month.

FIG. 3 illustrates example 300 of pre-defined criteria for rating speech effectiveness, in accordance with an embodiment of the present invention. In this embodiment, each type of speech problem is given a weight factor based on the speaking mode. A threshold basis is defined for each speech problem, and a threshold or rating is calculated for each speech problem.

Example 300 includes table 302 and table legend 304. Column 310 of table 302 lists speech problems defined in the present embodiment. In another embodiment, a user may edit the list to include other problems or exclude items on the list that are not a concern for the user. The list includes speech problems that may be categorized as courtesy problems, presentation problems, emotional alarms, speech disfluencies, and background noise.

Column 320 of table 302 lists the weight of each speech problem by speaking mode. Column 320 is divided into three sub-columns, one for each of three speaking modes. In this example, the three speaking modes are "Group", "One on One", and "Presentation". The weights that are listed for each speech problem are defined as "1" for high importance, "2" for medium importance, and "3" for low importance, as shown in table legend 304. In some instances, a particular speech problem may not be applicable. For example, filibustering is not a problem if a speaker is giving a presentation. When a particular speech problem is not applicable, the weight is listed as "N/A". In another embodiment, the user may edit the weights attributed to each speech problem based on the user's particular situation or concerns.

Column 330 of table 302 lists the threshold basis. For the speech problems listed, there are two ways to measure an occurrence. A speech problem may be measured by how long the problem exists, in time. A speech problem may also be measured by the quantity of times the problem occurs over a defined base time period. In this example, the defined base time period is listed in table legend 304 as 5 minutes. The sub-column of column 330 labeled "Base Value" lists the definition of the occurrence of the problem, while the sub-column of column 330 labeled "Unit" describes how that occurrence is measured. For example, anger is measured by how long the problem exists. The threshold value for anger is 15 seconds. In another example, false starts are measured by the quantity of occurrences over the base time period. The threshold value for false starts is 2 incidents. In another embodiment, the user may edit the base value attributed to each speech problem, as well as the base time period, based on the user's particular situation or concerns.

Column 340 of table 302 lists the thresholds by speaking mode. The thresholds are the criteria speech analysis program 114 uses to determine whether there is relevant feedback for the user, as described with regards to step 214. In the depicted embodiment, the thresholds are calculated by multiplying the weight, from column 320, by the threshold base value, from column 330. The unit of the threshold remains the same as that shown in the sub-column of threshold basis column 330. For example, in group mode, the weight of mumbling is "2" and the threshold basis is "5 incidents". Therefore, by multiplying 2 times 5, the threshold for mumbling in group mode is 10 incidents. After 10 incidents, over a 5 minute time period, speech analysis program 114 notifies the user that the threshold has been met (step 216). In another example, in presentation mode, the weight of slow talking is "3" and the threshold basis is "15 seconds". Therefore, by multiplying 3 times 15, the threshold for slow talking in presentation mode is 45 seconds. After slow talking persists for 45 seconds, speech analysis program 114 notifies the user (step 216).

Figure 4:
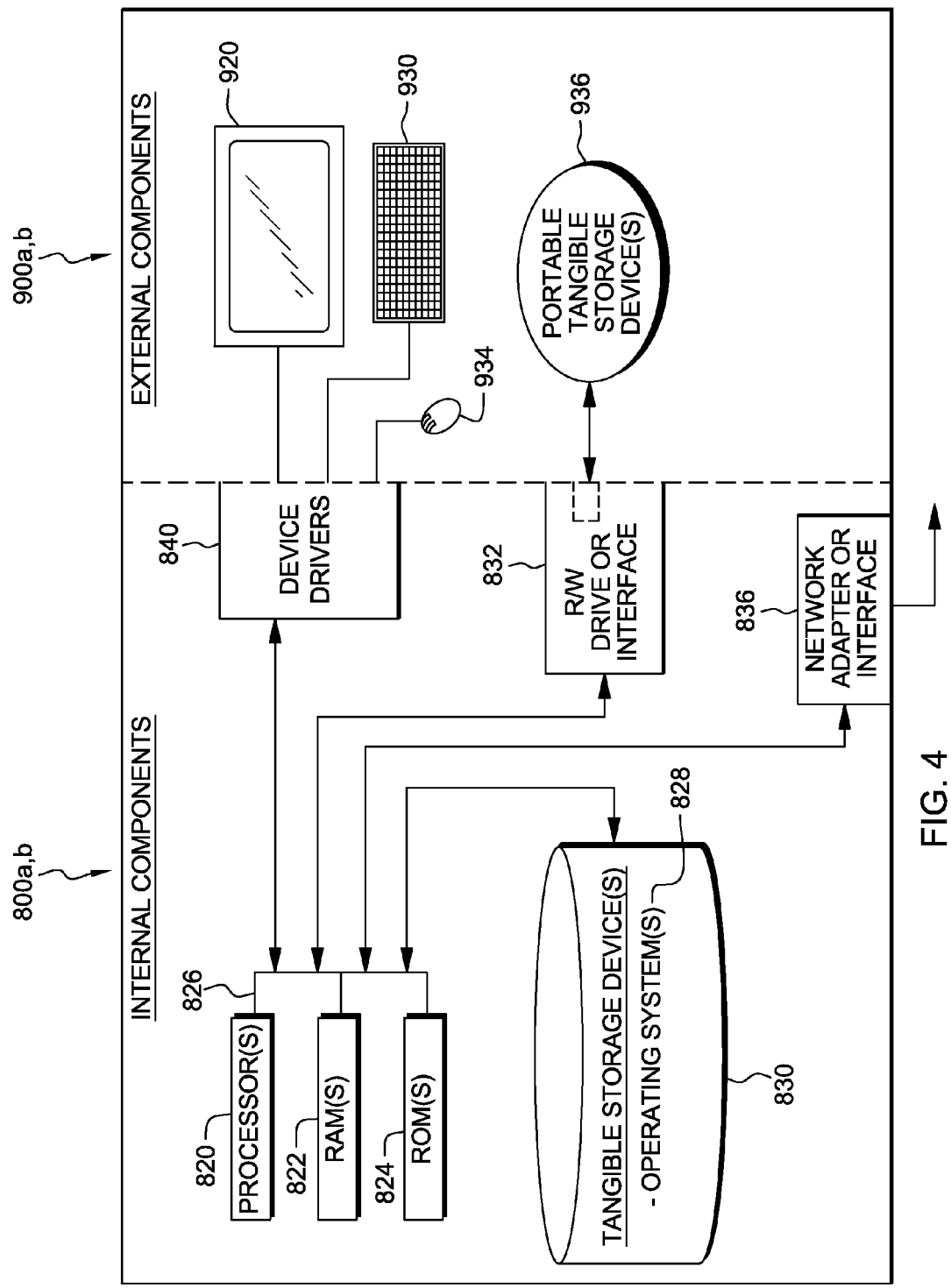
FIG. 4 depicts a block diagram of components of hardware and software within each of the computing devices of FIG. 1, in accordance with an embodiment of the present invention.

FIG. 4 depicts a block diagram of hardware and software within each of the computing devices of FIG. 1, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Computing/processing devices server computer 104 and computing device 108 include respective sets of internal components 800a,b and external components 900a,b, illustrated in FIG. 4. Each of the sets of internal components 800a,b includes one or more processor(s) 820, one or more computer readable RAM(s) 822 and one or more computer readable ROM(s) 824 on one or more buses 826, one or more operating system(s) 828 and one or more computer readable tangible storage device(s) 830. The one or more operating system(s) 828 and speech analysis program 114 in computing device 108 are stored on one or more of the respective computer readable tangible storage device(s) 830 for execution by one or more of the respective processor(s) 820 via one or more of the respective RAM(s) 822 (which typically include cache memory). In the illustrated embodiment, each of the computer readable tangible storage device(s) 830 is a magnetic disk storage device of an internal hard drive. Alternatively, each of the computer readable tangible storage device(s) 830 is a semiconductor storage device such as ROM(s) 824, EPROM, flash memory or any other computer readable storage device that can store but does not transmit a computer program and digital information.

Each set of internal components 800a,b also includes a R/W drive or interface 832 to read from and write to one or more portable computer readable tangible storage device(s) 936 that can store but do not transmit a computer program, such as a CD-ROM, DVD, memory stick, magnetic tape, magnetic disk, optical disk or semiconductor storage device. The program speech analysis program 114 in computing device 108 can be stored on one or more of the respective portable computer readable tangible storage device(s) 936, read via the respective R/W drive or interface 832 and loaded into the respective hard drive or computer readable tangible storage device(s) 830. The term "computer readable tangible storage device" does not encompass signal propagation media such as copper cables, optical fibers and wireless transmission media.

Each set of internal components 800a,b also includes a network adapter or interface 836 such as a TCP/IP adapter card or wireless communication adapter (such as a 4G wireless communication adapter using OFDMA technology). The program speech analysis program 114 in computing device 108 can be downloaded to the respective computing/processing devices from an external computer or external storage device via a network (for example, the Internet, a local area network or other, wide area network or wireless network) and network adapter or interface 836. From the network adapter or interface 836, the programs are loaded into the respective hard drive or computer readable tangible storage device(s) 830. The network may comprise copper wires, optical fibers, wireless transmission, routers, firewalls, switches, gateway computers and/or edge servers.

Each of the sets of external components 900a,b includes a display screen 920, a keyboard or keypad 930, and a computer mouse or touchpad 934. Each of the sets of internal components 800a,b also includes device drivers 840 to interface to display screen 920 for imaging, to keyboard or keypad 930, to computer mouse or touchpad 934, and/or to display screen for pressure sensing of alphanumeric character entry and user selections. The device drivers 840, R/W drive or interface 832 and network adapter or interface 836 comprise hardware and software (stored in computer readable tangible storage device(s) 830 and/or ROM(s) 824).

The programs can be written in various programming languages (such as Java®, C+) including low-level, high-level, object-oriented or non object-oriented languages. Alternatively, the functions of the programs can be implemented in whole or in part by computer circuits and other hardware (not shown).

Based on the foregoing, a computer system, method and program product have been disclosed for rating speech effectiveness. However, numerous modifications and substitutions can be made without deviating from the scope of the present invention. Therefore, the present invention has been disclosed by way of example and not limitation.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for determining speech effectiveness, the method comprising:
   receiving, by one or more computer processors, speech input;
   determining, by the one or more computer processors, based, at least in part, on the received speech input, a speaking mode of the received speech input, the speaking mode being one of: a conversation with words spoken by two or more people during a predetermined time interval, and a presentation with words spoken by one person and not any other person during a predetermined time interval;

detecting, by the one or more computer processors, at least one problem with the speech input;

if the speaking mode of the received speech input is determined to be a presentation and not a conversation, weighting the detected at least one problem with the speech input using a first factor while using the at least one or more computer processors, and, if the speaking mode of the received speech input is determined to be a conversation and not a presentation, weighting the detected at least one problem with the speech input using a second factor while using the at least one or more computer processors; and notifying a user, by the one or more computer processors, of the detected at least one problem with the speech input, if a rate of occurrence of the detected at least one problem exceeds a pre-defined threshold of the at least one problem with the speech input, wherein the rate of occurrence is based on the weighting of the at least one problem with the speech input and a base value of occurrence of the at least one problem with the speech input.

2. The method of claim 1, further comprising:

performing, by the one or more computer processors, an analysis of the detected at least one problem with the speech;

storing, by the one or more computer processors, the analysis of the detected at least one problem;

receiving, by the one or more computer processors, a request for feedback from a user;

responsive to receiving, by the one or more computer processors, a request for feedback from the user, retrieving, by the one or more computer processors, the analysis of the detected at least one problem;

determining, by the one or more computer processors, based, at least in part, on the request for feedback and the analysis of the detected at least one problem, feedback for the user; and providing, by the one or more computer processors, the feedback associated with the analysis of the detected at least one problem to the user.

3. The method of claim 2, wherein feedback includes a rating of speech effectiveness based, at least in part, on whether the speaking mode of the received speech input is a conversation with words spoken by two or more people during a predetermined time interval or if the speaking mode of the received speech input is a presentation with words spoken by one person and not any other person during a predetermined time interval.

4. The method of claim 1, wherein the detected at least one problem with the speech input belongs to a category, including at least one of: a courtesy problem, a presentation problem, an emotional alarm, one or more speech disfluencies, and a background noise.

5. The method of claim 1, further comprising:

determining, by the one or more computer processors, whether a first speaking mode of the received speech input has changed, wherein a speaking mode of the received speech input is one of a conversation and a presentation;

responsive to determining, by the one or more computer processors, the first speaking mode of the received speech input has changed, determining, based on the received speech input, by the one or more computer processors, a second speaking mode of the received speech input;

detecting, by the one or more computer processors, based, at least in part, on the second speaking mode of the received speech input, at least one problem with the speech input;

determining, by the one or more computer processors, based, at least in part, on the second speaking mode of the received speech input and the detected at least one problem with the speech input, whether the rate of occurrence of the detected at least one problem with the speech input exceeds the pre-defined threshold of the at least one problem with the speech input; and responsive to determining, by the one or more computer processors, that the rate of occurrence of the detected at least one problem with the speech input exceeds the pre-defined threshold of the at least one problem with the speech input, notifying, by the one or more computer processors, the user.

6. The method of claim 5, wherein the first factor and the second factor are based, at least in part, on the speaking mode of the received speech input and a level of importance of the detected at least one problem associated with the speech input.

7. A computer program product for determining speech effectiveness, the computer program product comprising:

one or more computer readable tangible storage devices and program instructions stored on the one or more computer readable tangible storage devices, the stored program instructions comprising:

program instructions to receive speech input;

program instructions to determine, based, at least in part, on the received speech input, whether a speaking mode of the received speech input is one of: a conversation with words spoken by two or more people during a predetermined time interval, and a presentation with words spoken by One person and not any other person during a predetermined time interval;

program instructions to detect at least one problem with the speech input;

if the speaking mode of the received speech input is determined to be a presentation and not a conversation, program instructions to weight the detected at least one problem with the speech input using a first, and, if the speaking mode of the received speech input is determined to be a conversation and not a presentation, program instructions to weight the detected at least one problem with the speech input using a second factor; and program instructions to notify a user of the detected at least one problem with the speech input, if a rate of occurrence of the detected at least one problem exceeds a pre-defined threshold of the at least one problem with the speech input, wherein the rate of occurrence is based on the weighting of the at least one problem with the speech input and a base value of occurrence of the at least one problem with the speech input.

8. The computer program product of claim 7, further comprising:

program instructions to perform an analysis of the detected at least one problem with the speech input;

program instructions to store the analysis of the detected at least one problem;

program instructions to receive a request for feedback from a user;

responsive to receiving a request for feedback from the user, program instructions to retrieve the analysis of the detected at least one problem;

program instructions to determine, based, at least in part, on the request for feedback and the analysis of the detected at least one problem, feedback for the user; and program instructions to provide the feedback associated with the analysis of the detected at least one problem to the user.

9. The computer program product of claim 8, wherein feedback includes a rating of speech effectiveness based, at least in part, on whether the speaking mode of the received speech input is a conversation with words spoken by two or more people during a predetermined time interval or if the speaking mode of the received speech input is a presentation with words spoken by one person and not any other person during a predetermined time interval.

10. The computer program product of claim 7, wherein the detected at least one problem with the speech input belongs to a category, including at least one of: a courtesy problem, a presentation problem, an emotional alarm, one or more speech disfluencies, and a background noise.

11. The computer program product of claim 7, further comprising:
   program instructions to determine whether a first speaking mode of the received speech input has changed, wherein a speaking mode of the received speech input is one of a conversation and a presentation;
   responsive to determining the first speaking mode of the received speech input has changed, program instructions to determine, based on the received speech input, a second speaking mode of the received speech input;
   program instructions to detect, based, at least in part, on the second speaking mode of the received speech input, at least one problem with the speech input;
   program instructions to determine, based, at least in part, on the second speaking mode of the received speech input and the detected at least one problem with the speech input, whether the rate of occurrence of the detected at least one problem with the speech input exceeds the pre-defined threshold of the at least one problem with the speech input; and
   responsive to determining that the rate of occurrence of the detected at least one problem with the speech input exceeds the pre-defined threshold of the at least one problem with the speech input, program instructions to notify the user.

12. The computer program product of claim 11, wherein the first factor and the second factor are based, at least in part, on the speaking mode of the received speech input and a level of importance of the detected at least one problem associated with the speech input.

13. A computer system for determining speech effectiveness, the computer system comprising:
   one or more computer processors;
   one or more computer readable storage media;
   program instructions stored on the computer readable storage media for execution by at least one of the one or more processors, the program instructions comprising:
   program instructions to receive speech input;
   program instructions to determine, based, at least in part, on the received speech input, a speaking mode of the received speech input, the speaking mode being one of: a conversation with words spoken by two or more people during a predetermined time interval, and a presentation with words spoken by one person and not any other person during a predetermined time interval;
   program instructions to detect at least one problem with the speech input;

if the speaking mode of the received speech input is determined to be a presentation and not a conversation, program instructions to weight the detected at least one problem with the speech input using a first factor, and, if the speaking mode of the received speech input is determined to be a conversation and not a presentation, program instructions to weight the detected at least one problem with the speech input using a second factor; and
   program instructions to notify a user of the detected at least one problem with the speech input, if a rate of occurrence of the detected at least one problem exceeds a pre-defined threshold of the at least one problem with the speech input, wherein the rate of occurrence is based on the weighting of the at least one problem with the speech input and a base value of occurrence of the at least one problem with the speech input.

14. The computer system of claim 13, further comprising:
   program instructions to perform an analysis of the detected at least one problem with the speech input;
   program instructions to store the analysis of the detected at least one problem;
   program instructions to receive a request for feedback from a user;
   responsive to receiving a request for feedback from the user, program instructions to retrieve the analysis of the detected at least one problem;
   program instructions to determine, based, at least in part, on the request for feedback and the analysis of the detected at least one problem, feedback for the user; and
   program instructions to provide the feedback associated with the analysis of the detected at least one problem to the user.

15. The computer system of claim 14, wherein feedback includes a rating of speech effectiveness based, at least in part, on whether the speaking mode of the received speech input is a conversation with words spoken by two or more people during a predetermined time interval or if the speaking mode of the received speech input is a presentation with words spoken by one person and not any other person during a predetermined time interval.

16. The computer system of claim 13, further comprising:
   program instructions to determine whether a first speaking mode of the received speech input has changed, wherein a speaking mode of the received speech input is one of a conversation and a presentation;
   responsive to determining the first speaking mode of the received speech input speech input type has changed, program instructions to determine, based on the received speech input, a second speaking mode of the received speech input;
   program instructions to detect, based, at least in part, on the second speaking mode of the received speech input, at least one problem with the speech input;
   program instructions to determine, based, at least in part, on the second speaking mode of the received speech input and the detected at least one problem with the speech input, whether the rate of occurrence of the detected at least one problem with the speech input exceeds the pre-defined threshold of the at least one problem with the speech input; and
   responsive to determining that the rate of occurrence of the detected at least one problem with the speech input exceeds the pre-defined threshold of the at least one problem with the speech input, program instructions to notify the user.

17. The computer system of claim 16, wherein the first factor and the second factor are based, at least in part, on the speaking mode of the received speech input and a level of importance of the detected at least one problem associated with the speech input.

* * * * *